United States Patent [19]

Wachtel et al.

[11] Patent Number: 5,393,532
[45] Date of Patent: Feb. 28, 1995

[54] PROCESS FOR PREPARING A PHENYLALANINE-FREE DIETARY PRODUCT IN DRAGEE OR TABLET FORM

[75] Inventors: Ursula Wachtel, Bad Homburg vd.H.; Friedrich Schweikhardt, Friedrichsdorf/Ts.-2; Erhard Tesmer, Offenburg/Baden, all of Germany

[73] Assignee: Milupa Aktiengesellschaft, Friedrichsdorf/Ts., Germany

[21] Appl. No.: 39,236

[22] PCT Filed: Aug. 26, 1992

[86] PCT No.: PCT/EP92/01966
 § 371 Date: Jun. 25, 1993
 § 102(e) Date: Jun. 25, 1993

[87] PCT Pub. No.: WO93/03633
 PCT Pub. Date: Mar. 4, 1993

[30] Foreign Application Priority Data

Aug. 26, 1991 [DE] Germany .............................. 4128260

[51] Int. Cl.$^6$ .......................... A61K 9/28; A61K 9/30; A61K 9/42; A61K 9/14
[52] U.S. Cl. ..................... 424/476; 424/474; 424/475; 424/489; 514/960; 426/72; 426/74; 426/454; 426/656; 426/657; 427/2.14; 427/2.22
[58] Field of Search ............... 424/474, 475, 476, 489, 424/441; 514/960; 426/72, 74, 454, 656, 657, 658; 427/2.14, 2.22

[56] References Cited

U.S. PATENT DOCUMENTS 3,764,703 10/1973 Bergstrom et al. ................ 514/419

FOREIGN PATENT DOCUMENTS

| | | |
|---|---|---|
| 0184999 | 6/1986 | European Pat. Off. . |
| 0198431 | 10/1986 | European Pat. Off. . |
| 0388237 | 9/1990 | European Pat. Off. . |
| 0488078 | 6/1992 | European Pat. Off. . |
| 2574254 | 6/1986 | France . |
| 863986 | 5/1952 | Germany . |
| 4128260 | 3/1993 | Germany . |
| 60-196166A | 11/1986 | Japan . |
| 2223925A | 4/1990 | United Kingdom . |

OTHER PUBLICATIONS

*Chemical Abstracts,* 98:142181g, Lieske et al., 1983.

*Primary Examiner*—Thurman K. Page
*Assistant Examiner*—Carlos Azpuru
*Attorney, Agent, or Firm*—Bacon & Thomas

[57] ABSTRACT

The invention pertains to a process for preparing a phenylalanine-free dietetic product comprising L-amino acids, and optionally comprising carbohydrates, minerals, trace elements and/or vitamins, for persons afflicted with phenylketonuria particularly adults, juveniles and pregnant women. The process comprises preparing a wet batch by dispersing in water the L-amino acids, some or all of the optional components, and at least one fatty material as an emulsifier, after which the wet batch is spray-dried. The spray-dried wet batch is then mixed with additional vitamins and/or carbohydrates and at least one fatty material as a separation agent to produce a mass. The mass thus produced is processed into cores for dragees or tablets, and the dragee or tablet cores are provided with coatings or dragee covers. The dietetic product is used as a nutrition supplement.

22 Claims, No Drawings

PROCESS FOR PREPARING A PHENYLALANINE-FREE DIETARY PRODUCT IN DRAGEE OR TABLET FORM

DESCRIPTION

The invention concerns a phenylalanine-free dietetic product based on amino acids, which is intended for persons, in particular children, adults and pregnant women who suffer from phenylketonuria, as well as to a process for preparing this phenylalanine-free dietetic product and a carrier to be used therewith.

Phenylketonuria belongs to genetically determined diseases representing disorders in which altered coding sequences of deoxyribonucleic acid determine the state of the disease. Because of genetic mutation, anomalous proteins are expressed. For example, the pathogenesis of enzymopathies (those diseases caused by reduced or absent enzyme activity) is based on the accumulation of the substrates left unmetabolized and their metabolites.

Presently eleven different mutations are known in the phenylalanine hydroxylase gene. When such mutation results in a complete lack of activity by such enzyme, then there will be a so-called phenylketonuria (hereafter PKU). If the enzyme effects only a reduced activity, then this condition leads to the so-called hyperphenylalanine anemias which must also be treated in part.

Because of the metabolic disorder, the phenylalanine accumulates in the body of the ailing person or patient and its concentration in the blood and tissue rises much above the normal range. As the concentration increases, the phenylalanine is then catabolized through metabolic bypasses ordinarily left unused by the body.

The increased level of phenylalanine in the plasma leads to a degradation of numerous metabolic mechanisms in the brain. If PKU is left untreated, children will incur brain immaturity with intellectual backwardness of varying degrees.

It was assumed until recently that by the onset of puberty, an increased level of phenylalanine no longer causes metabolic disorders in the brain. More recent investigations relating to young adults for whom treatment had been stopped during their school years, however, showed that there are be neurological disorders, such as measurable degradation of reaction times.

Phenylketonuria can be treated with food low in phenylalanine. As a result the patients develop normally physically and psychologically and can be educated. Moreover, they reach the age of reproduction in a problem-free manner and accordingly young female PKU patients are increasingly becoming pregnant.

In order to achieve normal intellectual and physical development of a PKU-afflicted child, the phenylalanine level in the plasma must be lowered by means of a low phenylalanine diet to normal values and must be stabilized there.

For that purpose such children receive diets with restricted amounts of protein and just as much phenylalanine as required by the child's body for protein build-up (growth). Accordingly, only such diets can be used which are inherently low in protein and hence also low in phenylalanine.

However, a diet low in phenylalanine by itself would deprive the child of sufficient amounts of other amino acids which are equally important for sustenance. Accordingly, children suffering from PKU require a protein source in addition to a phenylalanine-low diet, said source lacking phenylalanine but containing sufficient amounts of all other amino acids.

Special products already are known which are composed of protein constituents, particularly amino acids, but which do not contain phenylalanine. Vitamins, minerals and trace elements are additionally integrated into such mixtures because a PKU-afflicted child would not receive these nutrients in adequate amounts from the phenylalanine-low diet.

Presently, PKU patients are urged to sustain their phenylalanine-low diet throughout life, particularly in the case of pregnant PKU-women. Such groups of patients must observe the PKU diet as well as take the known special products.

It has been thought so far that protein metabolism requires the simultaneous presence of all, and hence also of the non-essential, amino acids. Therefore the known, conventionally used special products or phenylalanine-free mixtures of amino acids for infants and children with their high growing needs contain all amino acids except for the metabolically disordered phenylalanine.

Depending on the particular metabolism of a PKU patient, he has been required to ingest daily from 45 to 70 g of the known phenylalanine-free mixture of amino acids. This is a substantial quantity which inherently and much adversely affects the acceptance of these special products by the patients, especially juvenile ones.

The German patent application P 40 37 447.5, which was not pre-published, describes a phenylalanine-free dietetic product containing only specific amino acids. Thus the daily protein need of juvenile and adult PKU patients can be covered completely or nearly completely with a mixture of only certain specific amino acids. Thereby the daily ingested quantity can be reduced. The dietetic product described in said German patent application is in powder form.

Especially as regards adolescents, a diet and a dietetic product supporting said diet will be accepted in large part depending on peer attitude. PKU patients already suffer from the fact that keeping to the necessary diet does not include conventionally served foods. This is already noticed by the peer group.

In addition, such persons must take considerable quantities of a phenylalanine-free mixture of amino acids with their meals. The heretofore known mixtures of amino acids and the related special nutrients exude an alien and offensive odor which neighbors find repulsive. In addition, such mixtures of amino acids have a peculiar and unpleasant taste.

Because of these factors, many PKU patients discontinue their diet and thus fail to ingest the phenylalanine-free mixtures of amino acids, resulting in a rise in the level of phenylalanine level in the plasma, and allowing for the above-discussed disease disorders to occur.

The object of the present invention is to create a phenylalanine-free dietetic product which shall be more readily acceptable to PKU patients as well as the process for making such a product.

This object is obtained with respect to the process by the disclosure of claim 1 and with respect to the dietetic product by the disclosure of claim 9.

The invention prepares a phenylalanine-free dietetic product or phenylalanine-free mixture of amino acids, which contain all the amino acids required for nutrition or a part thereof, or only the essential amino acids, said product being free of the characteristic intrinsic taste and odor of the amino-acid mixtures known so far. The dietetic product of the invention moreover may contain vitamins, minerals and/or trace elements in order to ensure the supply of these essential nutrients.

The dietetic and phenylalanine-free product of the invention is present in the form of tablets or sweet-coated pills, i.e. dragees. The dragees or tablets are covered or sweet-coated so that the taste and the odor of the L-amino acids present in the cores of the tablet or dragee are not sensed by the patient.

Because the dragees are often consumed in everyday life, the coating ought to or must be free of pharmaceuticals. Accordingly drug substances should not be used. Rather the coating shall consist only of such substances which are compatible with foodstuffs. These substances too should be selected in such manner that, for improved compatibility, the dragees will completely disintegrate only in the small intestine.

Appropriately, a coating substance shall be selected which evinces a characteristic neutral or pleasant taste.

The cores of the dragees or tablets (hereafter dragee will denote both) appropriately are covered with sugar and additives allowed by law for such purposes. Therefore, only such substances shall be used in Germany which are authorized under the foodstuff acts and the law for necessary articles. The dragee cover should mask the odor and the taste of the amino acids or of the mixture of active ingredients in such manner that the dragees will be neutral to the taste.

The dragee dietetic product of the invention represents extraordinary relief for PKU patients following a long-term and possibly a life-long diet.

The dragees can be ingested easily and in a problem-free manner throughout the day in conjunction with water, tea, juices or similar beverages prescribed by the physician. This eliminates preparation by dissolving powders and granules in liquids as has been required heretofore by the known special products. Therefore usage is simple, dosing is reliable, and the level of the plasma phenylalanine in the blood is easily set.

As regards pregnant patients, the dietetic product of the invention avoids energy loss associated with foodstuff loss caused by repeated vomiting. The neutral tasting dragees exhibit no emetic irritation of the kind generated by the heretofore known powder mixtures of amino acids; they are quite compatible and therefore reliable implementation of the PKU diet is possible during pregnancy.

In order to process the L-amino acids, and, where called for, any present or admixed carbohydrates, trace elements and/or vitamins, into dragees, it is essential that a fatty material acting as a separation agent be admixed to this mass, which as a rule is present in powder form. Therefore an object of the invention also is such a mass, i.e. such a half-finished material.

Provided that the dietetic product in dragee form includes such a fatty material in the dragee core, this core can then be fitted with a coating or dragee cover.

In the process of the invention, the L-amino acids and any minerals and/or trace elements are placed in water in step (a) and thereby are dissolved or dispersed. The wet batch so produced is then spray-dried. The spray product is then processed in step (d) into cores of dragees or tablets and next it is provided with a coating or a dragee cover in step (e).

It has been found that such a spray product presents substantial difficulties if it is processed without a separation agent, because otherwise caking arises in the tablet press. Therefore a fatty material is added to function as a separation agent.

The total quantity of this fatty material can be integrated into the mass which shall be processed into dragee cores by mixing this fatty material with the spray product made in stage (b).

Mono- and/or di-glycerides of high melting points and magnesium stearate have been found to be suitable separation agents, i.e. fatty materials. However, other fatty materials with separating properties also may be used.

In a further embodiment, the total quantity of fatty material can be included in the aqueous solution or dispersion in step A before spray drying. In that case the fatty material not only serves as a separation agent when tablets are being made, but it also improves the distribution of the constituents of the wet batch prior to spray drying and increases wetting. On that account emulsifiers with a high melting point (70° C.), fatty materials with high melting points or similar fatty materials shall be preferably used, which are allowed under law in the preparation of foodstuffs, in particular dietetic foodstuffs.

Preferably however a portion of the fatty material is added to the wet batch to be spray-dried, and another portion of the fatty material is mixed with the spray product. In the latter embodiment, a solid can be integrated into the wet batch, and this solid is different from the fatty material to be admixed to the spray product. Obviously a mixture of fatty materials may be used in all described modes of embodiments.

Again, any vitamins and/or carbohydrates present may be added as a whole to the wet batch or be mixed with the spray product. In this case also a portion of the vitamins and/or of the carbohydrates may be added to the wet batch and the remaining portion can be added to the spray product. Preferably the entire amount of the vitamins shall be added following the spray drying, i.e. it will be admixed with the spray product. In this procedure, the vitamins preferably are pre-mixed with one or more carbohydrates. In the latter instance further carbohydrates already may be added to the wet batch.

The carbohydrates may be from various origins. For technical reasons, however, preferably sugar, lactose, dextrose, maltodextrines and starch shall be used. The carbohydrates admixed to the tablet cores are tabletting accessories. Obviously, they too represent dragee cover substances.

The powder mixture or mass so made can be directly processed into tablets or be pressed. Preferably however the first steps are pre-compaction, granulation, whereafter tablet or dragee cores are pressed, said cores thereupon being coated or fitted with a dragee cover.

In order to ensure smooth production, the powder mixture so made is preferably first pressed in a compactor (Hutt, Bepex) and this step is followed by granulation preferably in a Frewitt granulator or another suitable comminuting system.

Preferably again the processing of the powder mixture or of the mass to be processed into tablets shall be carried out in a room wherein the relative humidity is $\leq 30\%$ and in particular 20% or less.

When preparing the spray product, the pH value of the wet batch preferably shall be controlled not to drop below 6.3. Accordingly the pH value preferably shall be continuously monitored during production and where called for alkalinizing compounds, preferably a solution of potassium hydroxide or potassium carbonate shall be added to the wet batch to keep the pH value at least at 6.3.

The amino acids present in the dietetic product of the invention or the amino acids used in the process of the invention may be present in any suitable form, especially in any form appropriate for foodstuffs. Illustratively the amino acids may be present in the form of salts, hydrochlorides, hydrates, acetates and maleates etc. Again the amino acids may be used in the form of dipeptides as long as these dipeptides do not contain phenylalanine.

Because L-glutamic acid and L-aspartic acid are amino acids reacting in a very acid manner, they are preferably used in the form of the salts of K, Na or Mg or else as L-lysine-L-glutamate or L-arginine-L-glutamate, as otherwise the pH value of the wet batch may sharply drop to below 5.0. This would lead to significant instabilities and phase separations during wet-batch preparation. Moreover the amino acids are preferably added in a specific sequence to the wet batch because it is possible thereby to avert precipitations and inhomogeneities by settling when making the spray product. Illustratively the following amino acids are added in the following sequence: sodium L-glutamate, L-arginine-L-glutamate, L-lysine-L-glutamate, K-L-aspartate, Mg-L-aspartate, L-proline, L-isoleucine, L-leucine, L-tyrosine, L-threonine, L-valine, L-alanine, L-methionine, L-cystine, L-histidine, L-glycine, L-tryptophane, L-serine.

In another preferred embodiment, cold water, especially between 3° and 15° C., is used to make the wet batch. To begin with, a viscosity-raising agent, such as guar, is dissolved in the cold water to prevent the settling of water-insoluble materials. Thereupon the amino acids and optionally any minerals and/or trace elements present and the desired portion of the carbohydrates are integrated. Next the wet batch is heated preferably to 70° to 90° C., more preferably to 75°–80° C. and most preferably to about 75° C. Thereupon the desired amount of fatty material is initially added. The reason for this procedure is as follows: It is known that sugar and amino acids already form browning products (Maillard reactions). To minimize these Maillard reactions, the batch is prepared cold as stated above, and it will be heated only prior to adding the fatty materials or emulsifiers. Therefore it is important that the fatty materials or emulsifiers be introduced into the hot batch only at the end.

Hence the phenylalanine-free dietetic product of the invention preferably shall be prepared in such manner that all L-amino acids, any present minerals and/or trace elements, a portion of the fatty materials or emulsifiers and of the carbohydrates, are placed in water and thereby are dispersed, dissolved or emulsified. Preferably the parameters of pH value, temperature and sequence described above shall be observed. Thereupon the process includes homogenization to achieve a concentrate which is as uniform, smooth, viscous and homogeneous as possible. The next step is pasteurization, appropriately using a blade heater resulting in a large reduction of germs in the concentrate. Then the product is homogenized and dried on a spray tower, preferably with nozzles. The spray product is mixed with the mixture of vitamins (preferably the entire mixture) which preferably was premixed in a portion of the carbohydrates being used. This powder mixture is then mixed with preferably a portion of the present fatty materials to be used.

It has been found that the return of the cyclone powder and part of the spray powder into the spray tower should be kept as low as possible to avoid adhesion and excessive instantization. The powder so prepared is quite flowing.

The powder or granulate used to prepare the cores of the dragees or tablets can be processed in tablet presses (rotary presses, excentric presses and the like) into tablet cores without causing caking.

These cores then are coated with sugar and gelatinizers such as pectin and gum arabicum. Preferably the hygroscopic tablet cores are carefully insulated before depositing the dragee cover because otherwise cracks in said cover may occur during storage.

Preferably fatty substances such as Boeson VP and also gelatinizers are used to insulate the cores. These substances also act as bonding agents for the dragee cover. Preferably, additives allowed under the laws of foodstuffs and necessary articles shall be used when making the dragee cover.

It has been found that a tear-proof dragee cover can be achieved using sugar and gelatinizers such as pectin and gum arabicum. This dragee cover is neutral to the taste or sweet when held in the mouth and completely masks the inherent odor of the pharmaceutically effective substances.

Preferably the dragees are made in a weight of 700 to 800 mg, the content of effective substances (amino acids plus other core constituents) amounting to 400 mg.

The number of dragees to be ingested depends on the quantity of effective substance which must be ingested daily; it can be between 15 and 40 dragees a day.

The phenylalanine-free dietetic product of the invention or prepared in the manner of the invention is a food supplement with medically prescribed doses. Accordingly the product need not be enriched with fat.

The invention is elucidated below by means of preferred implementations discussed in the Examples.

EXAMPLE 1: Preparing a phenylalanine-free dietetic product in dragee form
TABLE A: recipe
TABLE B: recipe for spray product

| | A % Wt | B % Wt |
|---|---|---|
| L-Histidine | 1.708 | 1.716 |
| L-Isoleucine | 4.270 | 4.291 |
| L-Leucine | 7.212 | 7.247 |
| L-Lycine-L-Glutamate | 11.673 | 1.729 |
| L-Methionine | 1.708 | 1.716 |
| L-Threonine | 3.417 | 3.433 |
| L-Tryptophane | 1.329 | 1.335 |
| L-Valine | 5.124 | 5.149 |
| L-Alanine | 2.942 | 2.956 |
| A-Arginine-L-Glutamate | 4.840 | 4.863 |
| Magnesium-L-Aspartate | 1.993 | 2.003 |
| L-Cystine | 1.708 | 1.716 |
| Na-L-Glutamate | 9.130 | 9.174 |
| L-Glycine | 1.708 | 1.716 |
| L-Proline | 6.738 | 6.770 |
| L-Serine | 3.796 | 3.814 |
| L-Tyrosine | 5.694 | 5.721 |
| Potassium aspartate | 7.160 | 7.194 |
| Vanillin | 0.076 | 0.076 |
| Guar | 0.949 | 0.954 |
| Monoglycerides (emulcifier) | 0.949 | 0.954 |
| Potassium chloride | 0.995 | 1.000 |
| Potassium hydrogen phosphate | 1.624 | 1.632 |
| Magnesium hydrogen phosphate | 1.692 | 1.700 |
| Sodium hydrogen phosphate | 1.054 | 1.059 |

-continued
EXAMPLE 1: Preparing a
phenylalanine-free dietetic product in dragee form
TABLE A: recipe
TABLE B: recipe for spray product

|  | A<br>% Wt | B<br>% Wt |
| --- | --- | --- |
| Iron sulfate (II) | 0.099 | 0.099 |
| Copper-II acetate | 0.011 | 0.011 |
| Zinc sulfate | 0.062 | 0.062 |
| Manganese sulfate | 0.014 | 0.014 |
| Potassium iodide | 0.00036 | 0.00036 |
| Ammonium heptamolybdate | 0.00084 | 0.00084 |
| Magnesium citrate | 1.40300 | 1.41000 |
| Myo-inosite | 0.28500 | 0.28600 |
| Chorine hydrogen tartrate | 0.51700 | 0.51700 |
| Vitamin mixture | 0.47700 | — |
| Sugar | 7.64180 | 7.67980 |
|  | 100.00000 | 100.00000 |

First a spray-dried intermediate product is formed from those components except the vitamin mixture. Column B shows the %-by-weight composition of the spray product.

1.1 97 liters of cold water are fed into a heatable mixing tank with intensive agitation (Y-Stral, Ultraturrax) to prepare a 100 kg batch.

954 g of guar are entirely dissolved in this cold water. Thereupon 1 kg of potassium chloride is pre-dissolved in about 3 liters of warm water and added to the guar solution.

Potassium hydrogen phosphate and sodium dihydrogen phosphate are separately pre-dissolved each in about 6.5 liters of water and are sequentially added to the batch. Thereupon myo-inosite is pre-dissolved in about 3 liters of water and added to the batch. The batch is intensively agitated and is pumped in circulatory manner.

Sodium L-glutamate is thereupon incorporated into the batch using a venturi tube. The pH value of the solution is monitored and should be between 6.6 and 7.0.

Next, using a venturi tube, the raw materials below are sequentially incorporated with intensive agitation.

| 1 | 2 |
| --- | --- |
| L-arginine-L-glutamate | L-threonine |
| L-lysine-L-glutamate | L-alanine |
| Potassium L-aspartate | L-methionine |
| Magnesium L-aspartate | L-cystine |
| L-proline | L-histidine |
| L-isoleucine | L-glycine |
| L-leucine | L-tryptophane |
| L-tyrosine | L-serine |
| L-valine | Magnesium hydrogen phosphate |
|  | Magnesium citrate |

The iron sulfate is pre-dissolved in 2 liters of water and added to the batch. Copper acetate is dissolved in about 300 ml water and added to the batch. Zinc sulfate is pre-dissolved in about 650 ml water and added to the batch.

Manganese sulfate is pre-dissolved in 650 ml water and added to the batch. Potassium iodide and ammonium heptamolybdate are each separately pre-dissolved in about 60 ml hot water (60° C.) and are sequentially added to the batch.

The entire batch is heated with intensive stirring to 75° C. and simultaneously it is pumped in a circulatory manner.

The bath pH value moves between 6.3 and 6.5 Should the pH value drop below 6.3, 1-n potash lye or a 10% potassium carbonate solution is added until the pH becomes equal to or larger than 6.3. The emulsifier is molten in a water bath in a separate vessel and added to the batch which should be at 75° C.

Vanillin and sugar are integrated into the batch using a venturi tube.

Choline hydrogen tartrate is dissolved in about 3 liter of hot water (60° C.) and added to the batch. Resumed pH monitoring shows that it does not drop below 6.3. But if it should happen, buffering to a value of 6.3–6.5 pH by means of potash lye or potassium carbonate solution will be carried out. Thereupon the entire batch is heated to 75° C. and agitated for 10 min.

Thereupon homogenization is carried out in two steps (step 1: 150 bars; step 2: 50 bars). The concentrate evinces a dry mass of about 45% and is pumped into a heated reservoir and agitated intensively to prevent settling This is followed by post-heating using a blade heater to 75°–80° C. and by a second homogenization at 70–100 bars.

The concentrate is dried by means of a spray tower, the drying preferably being carried out using two nozzles.

| CONDITIONS | |
| --- | --- |
| entry temperature | 180–190° C. |
| exit temperature | 90–95° C. |
| nozzle pressure | 150 bars (120–150 bars) |
| residual moisture | max. 2.5° C. |
| powder temperature | max. 25° C. |

About 15–30% of the dried powder are again introduced into the spray region of the tower during the spray procedure. This mechanism is kept slight to avert excessive instantization.

The product prepared in the above described manner is quite flowing. It is packed and stored until further processing in polyethylene/paper bags.

1.2 Immediately following spray drying, the spray product so prepared is mixed with the mixture of vitamins:

| MIXING RECIPE | |
| --- | --- |
| spray product | 99.523% |
| vitamin mixture | 0.477% |
| Total | 100.000% |

As regards a 100 kg mixture, 99.523 kg of spray product and 0.4777 kg of vitamin mixture are weighed and are mixed for instance in a NAUTA mixer.

Thereupon the mixed product or the mass so obtained is packed and stored in polyethylene/paper bags or suitable evacuable containers until further processing.

1.3 The mixture or mass made in 1.2 is mixed with a monoglyceride of high melting point or with other suitable fatty materials of high melting points (for instance Boeson VP, Tegomuls) serving as separation agents in a Loedige mixer.

| MIXING RECIPE: | |
| --- | --- |
| spray product + vitamin mixture<br>(= effective substance mixture) | 98% |
| separation fat (for instance Boeson VP, Tegomuls) | 2% |
| Total | 100% |

The mixing time in the Loedige mixer is 5–10 min. Thereupon the mixture is compacted using a compactor (Hutt, Bepex) and is processed into a granulate using a Frewitt granulator.

The granulate is pressed by a tablet press (for instance Kilian rotary press, Fette rotary press) into tablet cores with weights of 408–412 mg (corresponding to 400 mg of effective-substance mixture).

1.4 SWEET-COATING

The tablet cores are surface-treated in a sweet-coating vessel by means of fatty substances (for instance Boeson VP) and then are coated with sugar, pectin and gum arabicum.

| WEIGHT PER DRAGEE | |
|---|---|
| gum arabicum | 3.000 mg |
| sugar | 283.500 mg |
| pectin | 1.420 mg |
| Boeson VP (separation fat) | 0.080 mg |
| dragee cover | 288.000 mg |
| core weight (tablet core) | 412.000 mg |
| TOTAL WEIGHT | 700.000 mg |

The dragees are made in sweet-coating vessels and the deposition substances are dried with warm air.

Packing is in blisters.

The dragees keep very well and are easily ingested even for substantial daily doses.

ANALYSIS 1 dragee = 700 mg, containing 400 mg of a mixture of pharmaceutically effective substances.

| | 100 g Dragees | 1 Dragee (= 700 mg) | per 1 g protein | per 100 kcal |
|---|---|---|---|---|
| protein | 37.6 g | 0.26 g | — | 11.0 g |
| protein equivalent (1.2 g amino acids = 1 g protein) | 45.1 g | 0.326 g | — | 13.0 g |
| fat | 2.2 g | 0.015 g | — | 0.6 g |
| carbohydrates | 43.9 g | 0.30 g | — | 13.0 g |
| ash | 6.8 g | 0.50 g | — | 2.0 g |
| residual moisture | 2.0 g | — | — | — |
| Energy kJ | 1469 | 10.1 | — | — |
| Energy kcal | 346 | 2.4 | — | — |
| Vitamin A | 0.7 mg | 0.005 mg | 0.019 mg | 0.2 mg |
| Vitamin $B_1$ | 1.0 mg | 0.007 mg | 0.027 mg | 0.3 mg |
| Vitamin $B_2$ | 1.0 mg | 0.007 mg | 0.027 mg | 0.3 mg |
| Vitamin $B_6$ | 2.0 mg | 0.01 mg | 0.05 mg | 0.6 mg |
| Vitamin $B_{12}$ | 2.7 μg | 0.02 μg | 0.07 μg | 0.8 μg |
| Vitamin C | 54 mg | 0.4 mg | 1.4 mg | 15.6 mg |
| Vitamin $D_3$ | 6.4 μg | 0.05 μg | 0.17 μg | 1.9 μg |
| Vitamin E | 6.8 mg | 0.05 mg | 0.18 mg | 2 mg |
| Biotine | 98 μg | 0.7 μg | 2.6 μg | 28.3 μg |
| Ca—O—Pantothenate | 4.8 mg | 0.03 mg | 0.13 mg | 1.4 mg |
| Vitamin $K_1$ | 57 μg | 0.4 μg | 1.5 μg | 16.5 μg |
| folic acid | 354 μg | 2.5 μg | 9.4 μg | 102 μg |
| Niacinamide | 10 mg | 0.07 mg | 0.27 mg | 2.9 mg |
| Choline | 120 mg | 0.84 mg | 3.19 mg | 34.7 mg |
| Myo-Inositol | 1.62 mg | 0.011 mg | 0.04 mg | 0.47 mg |
| sodium | 730 mg | 5.1 mg | 19 mg | 211 mg |
| potassium | 1610 mg | 11.3 mg | 43 mg | 466 mg |
| calcium | 770 mg | 5.4 mg | 20 mg | 223 mg |
| magnesium | 310 mg | 2.2 mg | 8 mg | 90 mg |
| phosphorus | 460 mg | 3.2 mg | 12 mg | 133 mg |
| chlorine | 270 mg | 1.9 mg | 7 mg | 78 mg |
| zinc | 13 mg | 0.09 mg | 0.35 mg | 4 mg |
| copper | 2 mg | 0.01 mg | 0.05 mg | 0.06 mg |
| iodine | 150 μg | 1.1 μg | 4 μg | 43 μg |
| manganese | 2.6 mg | 0.02 mg | 0.07 mg | 0.08 mg |

| | 100 g Dragees | 1 Dragee (= 700 mg) | per 1 g protein | per 100 kcal |
|---|---|---|---|---|
| molybdenum | 260 μg | 1.8 μg | 7 μg | 75 μg |
| L-Isoleucine | 2.44 g | 0.02 g | 6.5 g | — |
| L-Leucine | 4.11 g | 0.03 g | 10.9 g | — |
| L-Lycine | 3.32 g | 0.02 g | 8.8 g | — |
| L-Methionine | 0.97 g | 0.007 g | 2.6 g | — |
| L-Phenylalanine | — | — | — | — |
| L-Tyrosine | 3.25 g | 0.02 g | 8.6 g | — |
| L-Threonine | 1.95 g | 0.01 g | 5.2 g | — |
| L-Tryptophane | 0.76 g | 0.005 g | 2.0 g | — |
| L-Valine | 2.92 g | 0.02 g | 7.8 g | — |
| L-Histidine | 0.97 g | 0.007 g | 2.6 g | — |
| L-Arginine | 1.50 g | 0.05 g | 4.0 g | — |
| L-Alanin | 1.68 g | 0.01 g | 4.5 g | — |
| L-aspartic acid | 4.13 g | 0.03 g | 11.0 g | — |
| L-cystine | 0.97 g | 0.007 g | 2.6 g | — |
| L-glutamic acid | 9.17 g | 0.06 g | 24.4 g | — |
| L-Glycine | 0.97 g | 0.07 g | 2.6 g | — |
| L-Proline | 3.84 g | 0.03 g | 10.2 g | — |
| L-Serine | 2.16 g | 0.02 g | 5.7 g | — |

EXAMPLE 2

Preparing a phenylalanine-free dietetic product in dragee form based solely on the essential amino acids.

| TABLE A: = recipe; TABLE B = spray-product recipe | | |
|---|---|---|
| | A Wt. % | B kg |
| emulsifier (monoglycerides) | 1.000 | 1.000 kg |
| guar | 0.900 | — |
| sugar | 1.850 | 1.854 kg |
| Vanillin | 0.050 | 0.050 kg |
| L-Lysinacetate | 15.000 | 15.075 kg |
| L-Histidine | 4.000 | 4.020 kg |
| L-Isoleucine | 8.800 | 8.844 kg |
| L-Leucine | 15.000 | 15.075 kg |
| L-Methionine | 3.500 | 3.518 kg |
| L-Threonine | 7.000 | 7.035 kg |
| L-Tryptophane | 2.800 | 2.814 kg |
| L-Valine | 11.000 | 11.055 kg |
| L-Tyrosine | 12.000 | 12.060 kg |
| mixture of minerals | 16.600 | 17.500 kg |
| mixture of vitamins | 0.500 | — |
| | 100.000 | 100.000% |

2.1 Preparing a 100 kg batch of spray product 100 liter of cold line-water are placed into a double-jacketed tank fitted with a Y-Stral or Ultraturrax agitator. Guar is completely dissolved in water using a venturi tube. Thereupon, by means of the venturi tube, the following are sequentially added:

| | |
|---|---|
| L-lysineacetate | L-threonine |
| L-isoleucine | L-methionine |
| L-leucine | L-histidine |
| L-tyrosine | L-tryptophane |
| L-valine | |

The batch is intensively agitated and pumped in circulatory manner.

Thereupon the mixture of minerals is pro-dissolved in 50 liter hot water (60° C.) and added to the batch. The batch is heated to 75° C. and is agitated at this temperature for 10 min.

The emulsifier is molten in water-bath at 70°–75° C. and added to the batch. Sugar together with vanillin is added through the venturi tube to the batch and is completely dissolved.

The batch is further processed and spray-dried as described in Example 1.

2.2 Immediately following spray drying, the spray product so prepared is mixed with the mixture of vitamins:

| MIXING RECIPE | |
|---|---|
| spray-product semi-finished product | 99.500% |
| vitamin mixture | 0.500% |
| Total | 100.000% |

For a mixture of 100 kg, 99.500 kg spray product and 0.500 kg vitamin-mixture are weighed and are mixed for instance in a Nauta-mixer for 20 min. Then the mixed product is interim-stored until further processing in suitable containers or polyethylene/paper bags.

Thereupon tabletting and sweet-coating is carded out as described in Example 1.

We claim:

1. A process for preparing a phenylalanine-free dietetic product comprising L-amino acids, and optionally comprising carbohydrates, minerals, trace elements and/or vitamins, for persons afflicted with phenylketonuria, wherein:
   (a) a wet batch is prepared by dispersing in water the L-amino acids, some or all of the optional components, and at least one fatty material as an emulsifier;
   (b) the wet batch is spray-dried,
   (c) the spray-dried wet batch is mixed with additional vitamins and/or carbohydrates and at least one fatty material as a separation agent to produce a mass;
   (d) the mass is processed into cores for dragees or tablets; and
   (e) the dragee or tablet cores are provided with coatings or dragee covers.

2. A process as claimed in claim 1 wherein vitamins are added in step (c), but not in step (a).

3. A process as claimed in claim 2 wherein the vitamins have been pre-mixed with a carbohydrate carrier.

4. A process for preparing a phenylalanine-free dietetic product comprising L-amino acids, and optionally comprising carbohydrates, minerals, trace elements, and/or vitamins, for persons afflicted with phenylketonuria, wherein:
   (a) the L-amino acids and the optional components of the dietetic product are added to cold water to produce a wet batch;
   (b) the wet batch is heated to 70°–90° C.;
   (c) a fatty material is added as an emulsifier to the heated wet batch;
   (d) the wet batch is spray-dried;
   (e) the spray-dried wet batch is mixed with additional vitamins and/or carbohydrates and at least one fatty material as a separation agent to produce a mass;
   (f) the mass is processed into cores for dragees or tablets; and
   (g) the cores are provided with coatings or dragee covers.

5. A process according to claim 4 wherein the cold water is at a temperature of 3° to 15° C. and has dissolved therein a viscosity raising substance or swelling means.

6. A process according to claim 5 wherein the viscosity raising substance or swelling means is guar.

7. A process according to claim 1 wherein the wet batch in step (a) is maintained at a pH of at least 6.3.

8. A process according to claim 7 wherein an alkalinizing means is added to the wet batch to control the pH.

9. A process according to claim 8 wherein the alkalinizing means is potassium hydroxide or potassium carbonate.

10. A process according to claim 1 wherein the wet batch of step (a) is homogenized prior to spray-drying.

11. A process according to claim 10 wherein the homogenized wet batch is then pasteurized and then re-homogenized prior to spray-drying.

12. A process according to claim 1 wherein the fatty material serving as an emulsifier and/or separation agent is a monoglyceride, a diglyceride or a triglyceride of a saturated fatty acid, or a mixture thereof.

13. A process according to claim 12 wherein the saturated fatty acid has a melting point above 65° C.

14. A process according to claim 1 wherein the L-amino acids are L-glutamic acids, L-aspartic acids, or a mixture thereof.

15. A process according to claim 1 wherein the L-amino acids which are added in step (a) are sodium L-glutamate, L-arginine-L-glutamate, L-lysine-L-glutamate, K-L-aspartate, Mg-L-aspartate, L-proline, L-isoleucine, L-leucine, L-tyrosine, L-threonine, L-valine, L-alanine, L-methionine, L-cystine, L-histidine, L-glycine, L-tryptophane and L-serine, and wherein said acids are added to the water in the above order.

16. A process according to claim 1 wherein core coatings or dragee covers comprise sugar, a gelatinizer, calcium carbonate, a fatty material as a separation agent, or a mixture thereof.

17. A process according to claim 16 wherein the gelatinizer is gum arabicum or pectin.

18. A phenylalanine-free dietary supplement for phenylketonurics which comprises:
    a core comprising L-amino acids and optionally comprising carbohydrates, minerals, trace elements, and/or vitamins; and
    a coating consisting essentially of sugar, a gelatinizer, and a fatty material as a separation agent, wherein the L-amino acids comprise from about 60% to about 80% by weight of the supplement.

19. A supplement according to claim 18 wherein the L-amino acids are L-isoleucine, L-leucine, L-lysine, L-methionine, L-tyrosine, L-threonine, L-tryptophane, L-valine, L-histidine, L-arginine, L-alanin, L-aspartic acid, L-cystine, L-glutamic acid, L-glycine, L-proline and L-serine.

20. A supplement according to claim 18 wherein the L-amino acids are the essential amino acids, except for phenylalanine.

21. A supplement according to claim 18 wherein the gelatinizer is gum arabicum or pectin.

22. A supplement according to claim 18 which contains less than 5% fat.

* * * * *